(12) United States Patent
Walavalkar et al.

(10) Patent No.: US 9,618,477 B2
(45) Date of Patent: Apr. 11, 2017

(54) DEVICES AND METHODS FOR SEQUENCING NUCLEIC ACIDS

(71) Applicant: California Institute of Technology, Pasadena, CA (US)

(72) Inventors: Sameer Walavalkar, Los Angeles, CA (US); Axel Scherer, Woodstock, VT (US); Thomas A. Tombrello, Altadena, CA (US); Aditya Rajagopal, Irvine, CA (US); Andrew P. Homyk, South Pasadena, CA (US); Erika Garcia, Los Angeles, CA (US)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 662 days.

(21) Appl. No.: 13/967,108

(22) Filed: Aug. 14, 2013

(65) Prior Publication Data

US 2013/0327645 A1  Dec. 12, 2013

Related U.S. Application Data

(62) Division of application No. 13/248,994, filed on Sep. 29, 2011, now Pat. No. 8,535,512.

(60) Provisional application No. 61/415,162, filed on Nov. 18, 2010, provisional application No. 61/405,019, filed on Oct. 20, 2010, provisional application No. 61/388,342, filed on Sep. 30, 2010.

(51) Int. Cl.
| | |
|---|---|
| G01N 27/447 | (2006.01) |
| C12Q 1/68 | (2006.01) |
| G01N 33/487 | (2006.01) |
| B82Y 30/00 | (2011.01) |

(52) U.S. Cl.
CPC ......... *G01N 27/447* (2013.01); *C12Q 1/6869* (2013.01); *G01N 33/48721* (2013.01); *B82Y 30/00* (2013.01)

(58) Field of Classification Search
CPC ......... G01N 33/48721; G01N 27/3278; C12Q 2565/631
See application file for complete search history.

(56) References Cited

U.S. PATENT DOCUMENTS

| 7,282,130 B2 * | 10/2007 | Flory ..................... B82Y 5/00 204/450 |
| 7,592,255 B2 | 9/2009 | Kuekes et al. |
| 2003/0116531 A1 | 6/2003 | Kamins et al. |

(Continued)

OTHER PUBLICATIONS

Sigalov et al. (Nano Letters 8/1, 2008, pp. 56-63) and supporting information.*

(Continued)

*Primary Examiner* — Matthew Martin
*Assistant Examiner* — Steven E Rosenwald
(74) *Attorney, Agent, or Firm* — Knobbe, Martens, Olson & Bear LLP

(57) ABSTRACT

Methods and devices for sequencing nucleic acids are disclosed herein. Devices are also provided herein for measuring DNA with nano-pores sized to allow DNA to pass through the nano-pore. The capacitance can be measured for the DNA molecule passing through the nano-pore. The capacitance measurements can be correlated to determine the sequence of base pairs passing through the nano-pore to sequence the DNA.

16 Claims, 14 Drawing Sheets

(56) References Cited

U.S. PATENT DOCUMENTS

| | | | |
|---|---|---|---|
| 2003/0222050 A1* | 12/2003 | Dugas | G01N 33/48721 216/2 |
| 2006/0003458 A1 | 1/2006 | Golovchenko et al. | |
| 2007/0190542 A1 | 8/2007 | Ling et al. | |
| 2008/0171316 A1* | 7/2008 | Golovchenko | C12Q 1/6869 435/6.11 |
| 2008/0187915 A1 | 8/2008 | Polonsky et al. | |
| 2010/0066348 A1 | 3/2010 | Merz et al. | |

OTHER PUBLICATIONS

Zhao et al. (Nano Letters 7/6, 2007, pp. 1680-1685).*
Clarke et al. (Nature Nanotechnology, 4, 2009, pp. 265-270).*
13248994-425429-EICSEARCH (in-house STIC search).
International Search Report and Written Opinion mailed on May 4, 2012 in PCT Application No. PCT/US2011/054074, filed Sep. 29, 2011.
Liu et al., "Self-Limiting Oxidation for Fabricating Sub-5 nm Silicon Nanowires", Appl. Phys. Lett., Mar. 14, 1994, vol. 64, No. 11, pp. 1383-1385.
Sigalov et al., "Detection of DNA Sequences Using an Alternating Electric Field in a Nanopore Capacitor", Dec. 11, 2007, Nano Letters, vol. 8, No. 1, pp. 56-63.

* cited by examiner

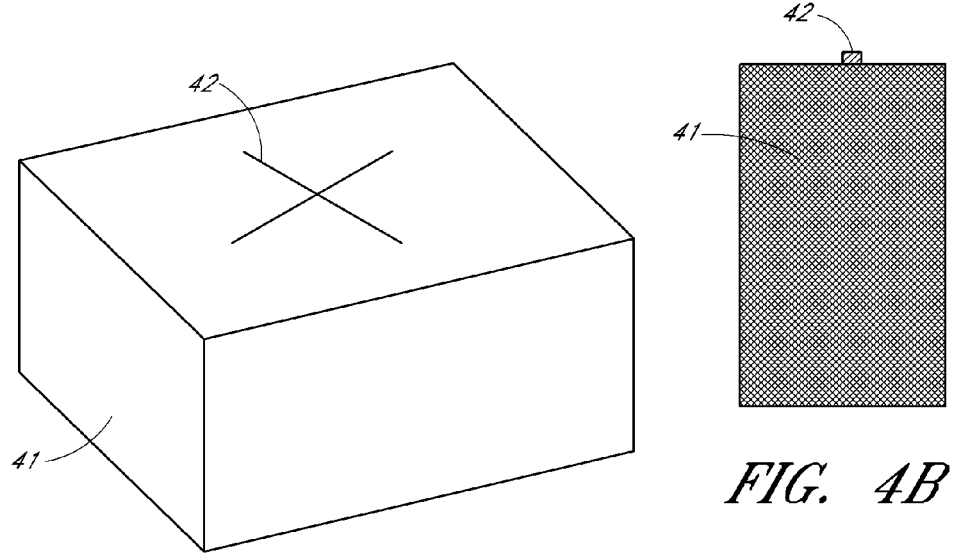
FIG. 4A
FIG. 4B
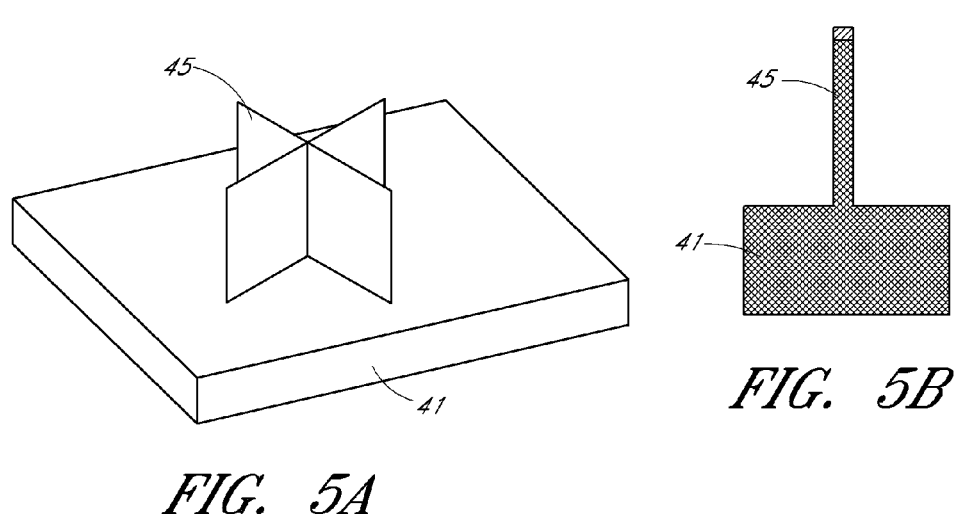
FIG. 5A
FIG. 5B

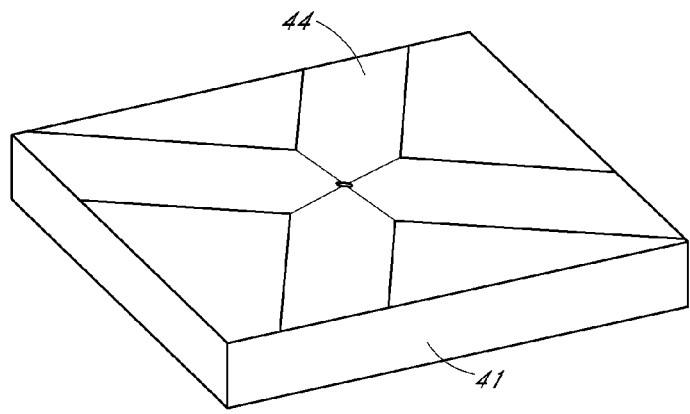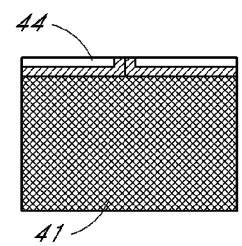
FIG. 8A    FIG. 8B
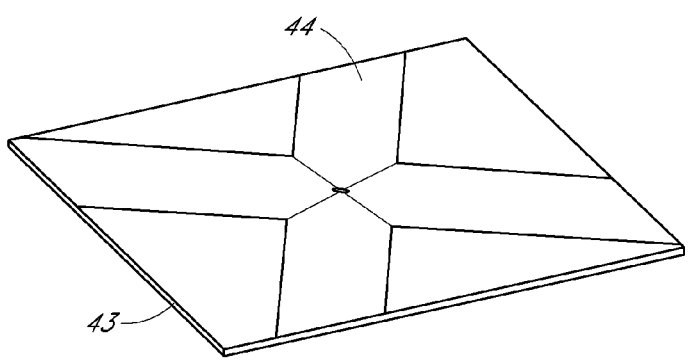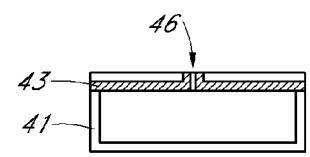
FIG. 9A    FIG. 9B

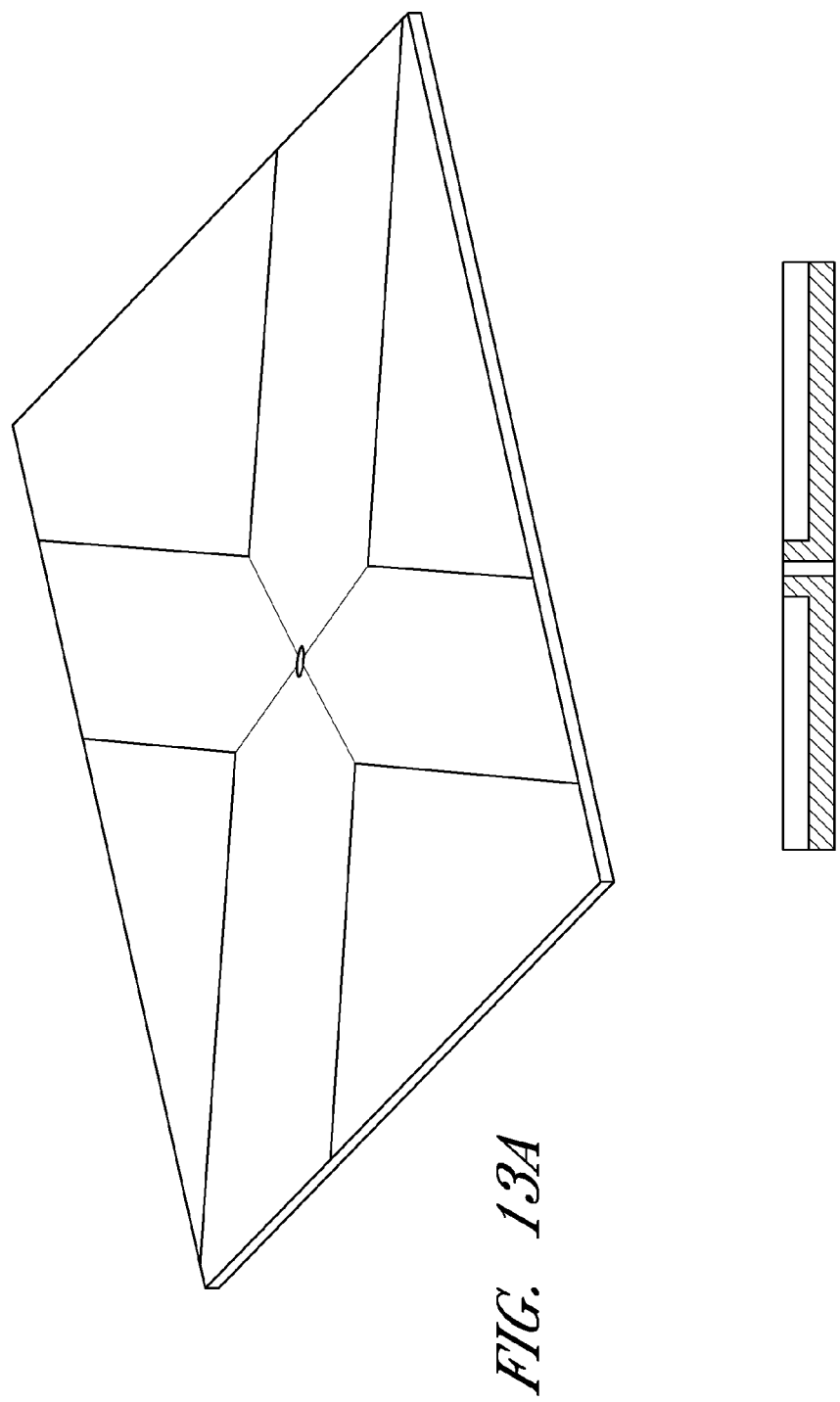

DEVICES AND METHODS FOR SEQUENCING NUCLEIC ACIDS

CROSS-REFERENCE TO RELATED APPLICATIONS

The present application claims priority as a divisional of U.S. Non-Provisional patent application Ser. No. 13/248,994 filed on Sep. 29, 2011, which claims priority to U.S. Provisional Patent Application Ser. Nos. 61/388,342 filed on Sep. 30, 2010; 61/405,019 filed on Oct. 20, 2010; and 61/415,162 filed on Nov. 18, 2010; each of which is incorporated by reference in their entirety.

STATEMENT REGARDING FEDERALLY SPONSORED R&D

This invention was made with government support under W911NF-07-1-0277 awarded by ARO-US Army Robert Morris Acquisition Center. The government has certain rights in the invention.

BACKGROUND OF THE INVENTION

Field of the Invention

The present application relates generally to fabricating porous substrates and their use in sequencing DNA.

Description of the Related Art

DNA sequencing includes methods and technologies that can be used to determine the order of nucleotide bases—adenine, guanine, cytosine, and thymine—in a molecule of DNA. Various methods known in the art for sequencing portions of DNA molecules are known and include chain termination methods with fluorescent dies and gel electrophoresis. Membrane based methods for sequencing DNA that measure the blocking current are also known in the art. DNA molecules have been measured by constructing pores in a thin membrane and electrophoretically pulling that DNA through the pore. The synthesis of such pores has been accomplished by using biological systems that generate pores through lipid bilayers with structures similar to the pores found in cell membranes or by using inorganic materials, such as graphene or silicon nitride. Measurement of the DNA and identification of individual polymerases is generally accomplished by measuring the "blocking current", which is the ion current that flows through the pores. The molecule can be held within the pore in a predictable way so that the shape and size can be determined through such blocking current. However, these methods have drawbacks such as slow measurement and noisy data. The data can have a lot of noise because the ion current is measured with a large series resistance using the electrolyte as the contact to the entrance and exit of the pore. The methods for measuring blocking current can also be inaccurate because the readings can depend on the orientation of the DNA strand as it passes through the pores. Also, multiple DNA strands can pass through the pore simultaneously and make the signal difficult to interpret for the desired strand of DNA.

SUMMARY OF THE INVENTION

Methods and apparatuses are provided herein for improved sequencing of nucleic acids.

In some embodiments methods for forming microelectronic devices are provided. The methods include providing a substrate comprising silicon, forming a silicon nano-pillar on the substrate, oxidizing the silicon nano-pillar to form an un-oxidized silicon core surrounded by silicon dioxide, forming a conductive layer on the silicon nano-pillar and substrate, removing a portion of the nano-pillar from the substrate to expose the silicon core, and selectively etching the remaining silicon core to form a pore in a top surface of the substrate. In some embodiments, the devices include conductive layers that are patterned to form electrodes. In some embodiments, the patterned electrodes form capacitors.

In some embodiments, methods for sequencing a nucleic acid are provided. The methods include providing a nucleic acid to be sequenced, passing the nucleic acid to be sequenced through a nano-pore on a substrate, the nano-pore having a diameter of less than about 5 nm, and measuring the capacitance across the pore as the nucleic acid passes through the nano-pore using one or more capacitors. In some embodiments the methods include correlating the capacitance measurements to known capacitance values for specific nucleic acids. In some embodiments the nucleic acids include single stranded DNA.

In some embodiments semiconductor devices are provided. The devices include a silicon substrate with a top surface having a nano-pore having a diameter of about 5 nm or less that is in fluid communication with an internal cavity in the silicon substrate, and a first and second top wire on the silicon substrate on opposing sides of the nano-pore. The devices can also include a first and second bottom wire on the silicon substrate orientated substantially perpendicular to the top wires on opposing sides of the nano-pore with the top and bottom wires separated by an insulator, with the top and bottom wires forming electrodes, and the electrodes forming a first, second, third, and fourth capacitor across the insulator where they intersect.

In some embodiments semiconductor devices are provided. The devices include a silicon substrate with a top surface having a nano-pore having a diameter of about 5 nm or less, and a first and second top wire on the silicon substrate on opposing sides of the nano-pore. In some embodiments the sample is pulled all the way through the substrate. The devices can also include a first and second bottom wire on the silicon substrate orientated substantially perpendicular to the top wires on opposing sides of the nano-pore with the top and bottom wires separated by an insulator, with the top and bottom wires forming electrodes, and the electrodes forming a first, second, third, and fourth capacitor across the insulator where they intersect.

BRIEF DESCRIPTION OF THE DRAWINGS

FIGS. 4-9 illustrate a substrate and cross-sections of a substrate during various steps for forming a device for sequencing DNA.

FIG. 4A illustrates a substrate with a hard mask. FIG. 4B illustrates a cross section of the substrate in FIG. 4A.

FIG. 5A illustrates a substrate with a nano-pillar. FIG. 5B illustrates a cross section of the substrate illustrated in FIG. 5A.

FIG. 8A illustrates the substrate of FIG. 7A after polishing to remove portions of the nano-pillar. FIG. 8B illustrates a cross section of the substrate of FIG. 7A.

FIG. 9A illustrates the substrate of FIG. 8A after etching to remove portions of the substrate. FIG. 9B illustrates a cross section of the substrate of FIG. 9A.

FIG. 13A illustrates a substrate with a patterned circuit. FIG. 13B is a cross section of the substrate of FIG. 13A.

DETAILED DESCRIPTION OF THE PREFERRED EMBODIMENT

Figure 1A:
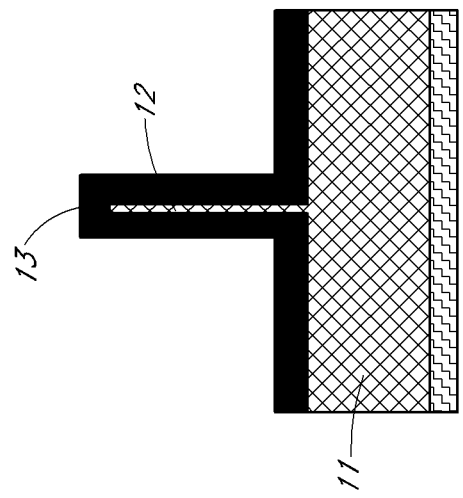
FIGS. 1A-1F illustrate cross-sections of a substrate during various steps for forming a device for sequencing DNA.

Improved methods and devices for sequencing nucleic acids are desired. Disclosed herein are methods and devices for sequencing nucleic acids, such as DNA. Sequencing can be accomplished through careful capacitance measurements of the individual nucleotides: adenine (A), cytosine (C), guanine (G), thymine (T), and uracil (U). Various methods for sequencing nucleic acids are known in the art. However, the processes suffer from many different problems such as being too slow and lacking precision and accuracy. Disclosed herein are methods and apparatuses with advantages that may include faster and more accurate sequencing.

Disclosed herein are methods and devices for measuring the capacitance of a nucleic acid or other molecule passing through a nano-pore formed in a substrate. Multiple electrodes on the substrate form capacitors that can be used to measure capacitance as a strand of DNA or other molecule passes through the pore. The capacitance measurements can then be correlated to the corresponding nucleotides or other molecule, e.g. protein or nano-particle.

Methods are also disclosed herein for forming the nano-pores on silicon substrates that can be used, for example, to sequence nucleic acids. The nano-pores can be sized to allow the molecule to be interrogated to pass through. For example, the nano-pores can be sized to allow a single strand of DNA to pass through the nano-pore. In other embodiments the nano-pore can be sized to allow double stranded DNA to pass through the nano-pore.

Methods are also disclosed herein for correlating electrical measurements, such as capacitance, for a nucleic acid passing through a nano-pore to the corresponding base pairs passing through the pore. Capacitance values for known sequences can be obtained separately, to provide a look-up table to be used in making the correlation and thus establishing the sequence. In this way the sequence of the nucleic acid can be determined. Similarly, other types of molecules or nano-particles can be identified in a sample by correlating the capacitance values as the sample passes through the nano-pore with measured capacitance values for known samples.

The methods disclosed herein can be applied to nucleic acids. In some embodiments denatured DNA is analyzed. In some embodiments single stranded DNA is analyzed. In some embodiments DNA is analyzed. In some embodiments denatured RNA is analyzed.

While the application focuses on sequencing DNA molecules, the methods and devices disclosed herein are applicable to identifying any type of molecule or nano-particle with dimensions smaller than 5 nm, for example proteins or gold nano-particles. The molecule or nano-particle can pass through the nano-pore while measuring the capacitance. The capacitance is then compared to a reference value or table to identify the molecule or nano-particle passing through the pore. The size of the nano-pore can be selected and fabricated based on the size of the molecule to be analyzed.

Fabrication of Devices for Sequencing DNA

Devices with nano-pores can be formed by the methods disclosed herein. In some embodiments, nano-pores can be formed on silicon substrates. In some embodiments, multiple nano-pores and multiple devices for sequencing nucleic acids are formed on the substrate. For example the devices can be spaced from about 100 nm to about 150 nm apart thereby allowing fabrication of an array of numerous devices for sequencing DNA on a single silicon substrate.

A silicon substrate can be patterned to form nano-pores having a desired size. First, a silicon substrate can be patterned and etched to leave raised silicon structures or nano-pillars having a desired size and shape. The silicon pillars can then be oxidized in a controlled manner to form silicon dioxide on the outer area of the silicon nano-pillars while leaving an un-oxidized portion of the nano-pillar at the center of the structure having a desired size. A conductive metal layer can be formed on the oxidized silicon substrate having a desired pattern. Next, a portion of the silicon nano-pillars can be removed using chemical or mechanical methods. A small portion of the silicon nano-pillars is left close to the surface of the substrate. Next, the remaining portion of the silicon nano-pillar is selectively etched to create a nano-pore having a desired size. The selective etch can also be used to etch a small internal cavity in the silicon substrate that is in fluid communication with a nano-pore. Additional conductive layers can be deposited on portions of the device to achieve a desired circuit pattern. The circuit can be designed such that it is capable of measuring electrical properties of the nucleic acids as they pass through the pore. The electrical property measurements can then be correlated to the corresponding nucleotides passing through the nano-pore to sequence the nucleic acid.

Figure 1B:
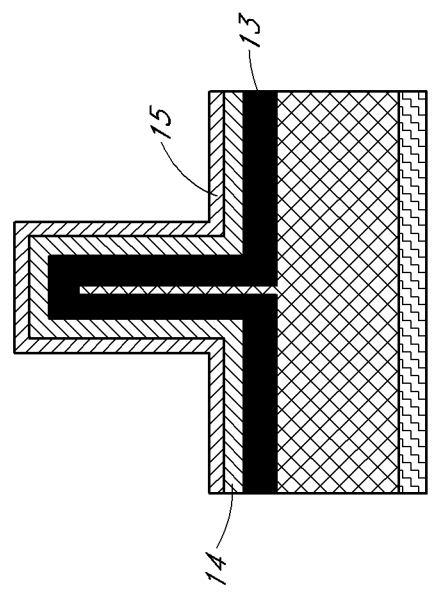
Figure 1C:
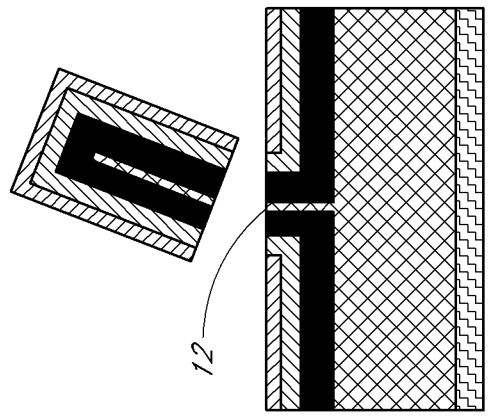
Figure 1D:
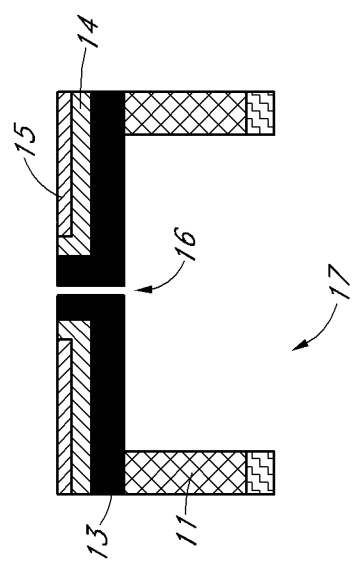
Figure 1E:
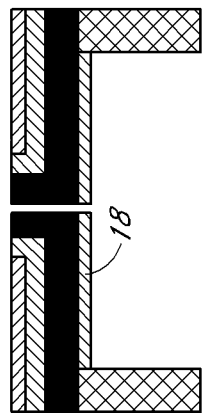
Figure 1F:
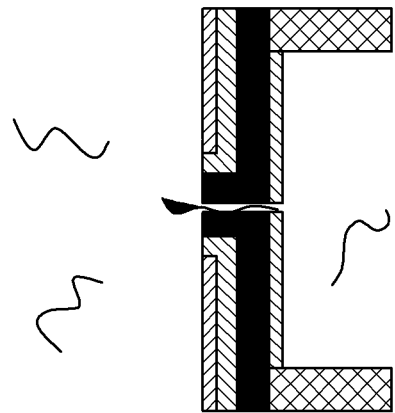
Figure 2:
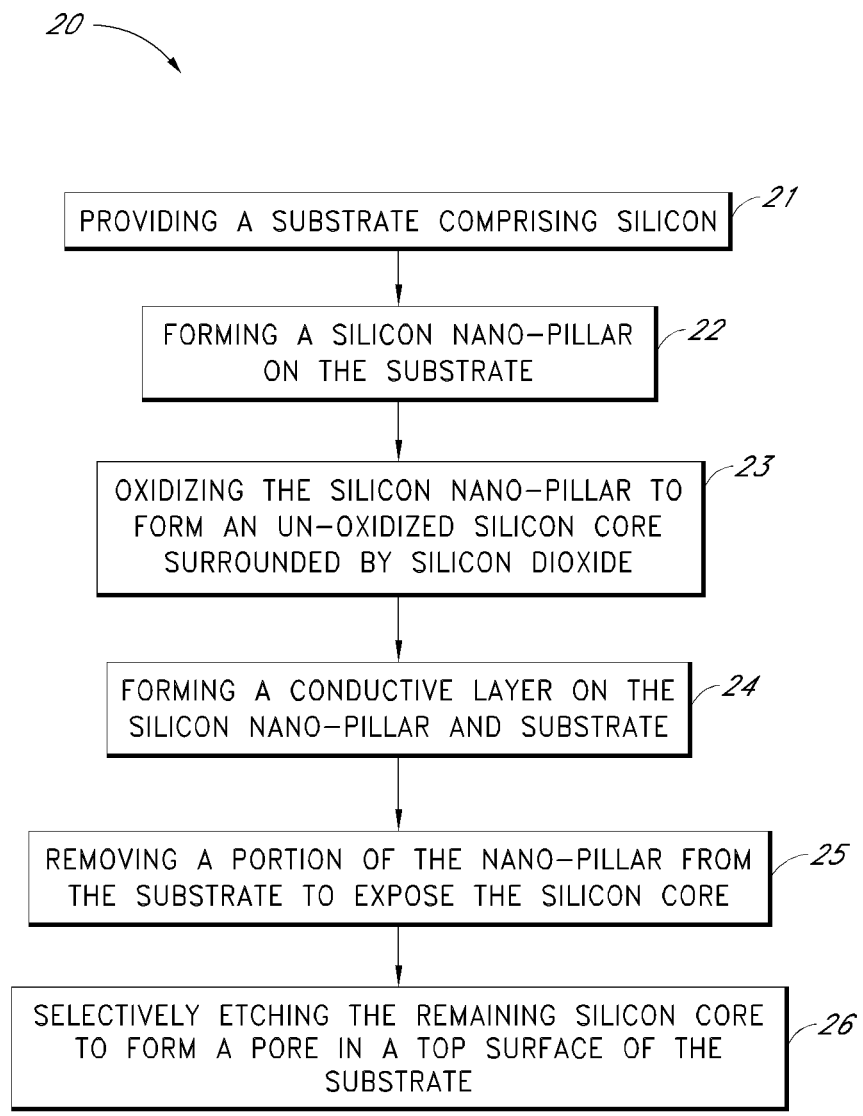
FIG. 2 illustrates a flow chart for a method for forming a device for sequencing DNA.

FIGS. 1A-1F illustrate cross-sections of a silicon substrate during various steps for forming a device for sequencing DNA. FIG. 2 illustrates a flow chart for a method for forming a device for sequencing DNA in one embodiment 20.

In some embodiments, a substrate comprising silicon is provided for processing 21. Silicon nano-pillars can be formed on the silicon substrate 22. In some embodiments the nano-pillars can be made from materials other than silicon that can be etched using methods disclosed herein.

Various methods can be used to pattern the substrate and form the nano-pillars, including photo-lithography and electron beam lithography. In some embodiments, the silicon wafer is patterned on a polished surface using photo or electron beam lithography to form nano-scale spots. Preferably, the patterns have a diameter of about 20 nm to about 50 nm. Next, a hard mask can be placed on the patterned surface using a lift-off process. In some embodiments, reactive sputter deposited aluminum oxide can be used as a hard mask. Next an electron beam is used to remove the resist. Next, the silicon can be etched using plasma etching techniques commonly employed in the microelectronics industry. The hard mask is then selectively removed leaving high-aspect-ratio silicon nano-pillars. In some embodiments the width of the nano-pillar is from about 20 nm to about 50 nm. The height of the nano-pillars is preferably from about 20 nm to about 50 nm.

Figure 3:
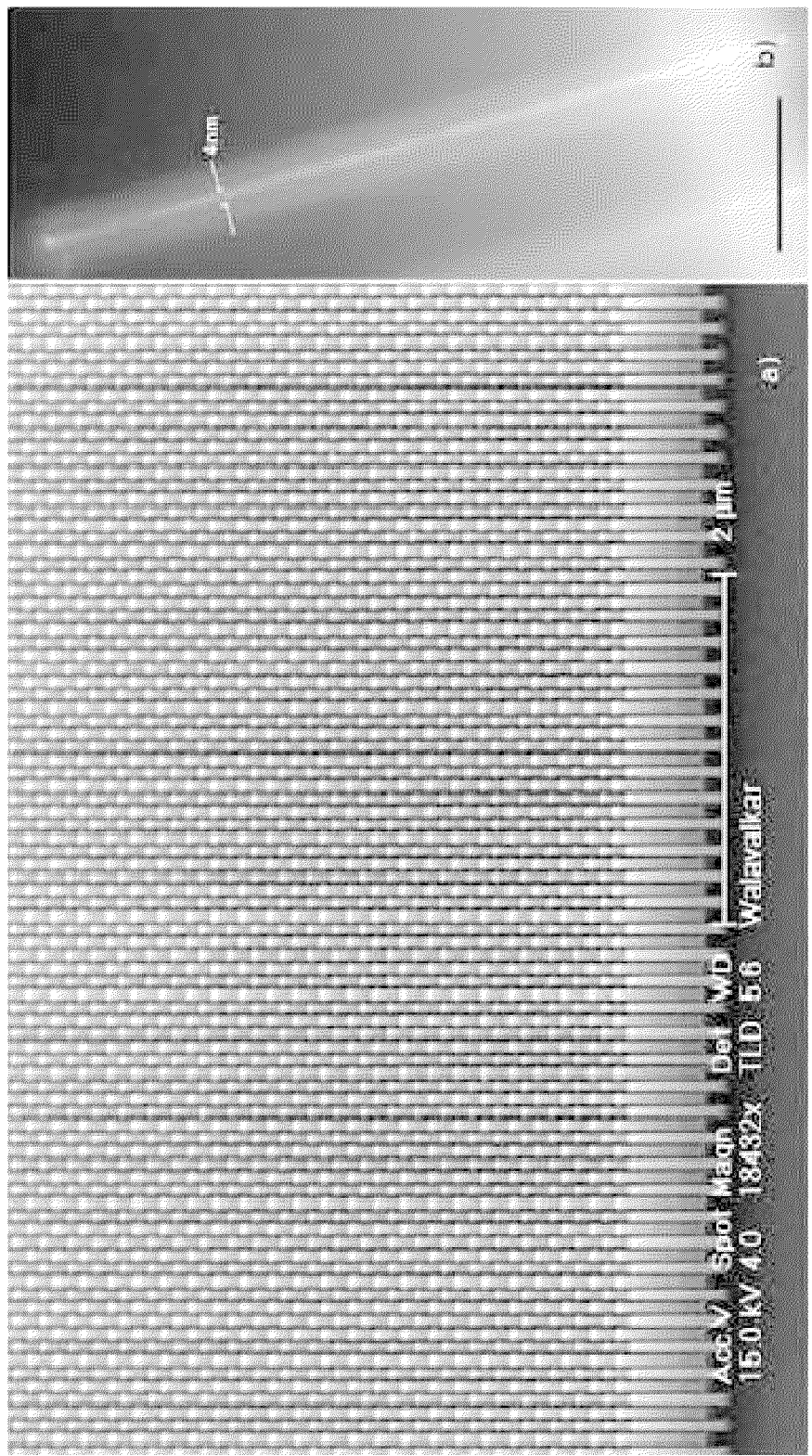
FIG. 3 shows an image of silicon nano-pillars formed by the methods disclosed herein.
Figure 6A:
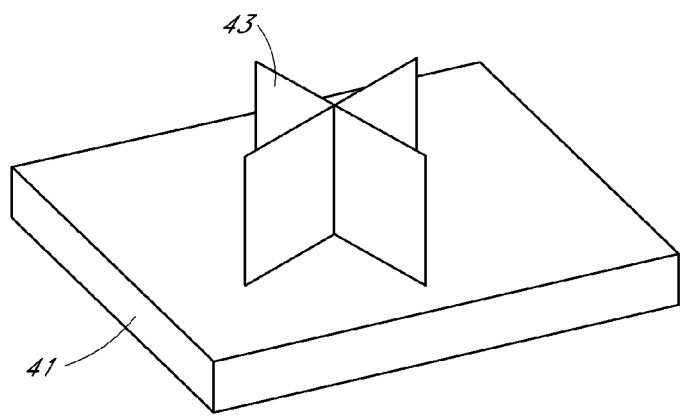
FIG. 6A illustrates a substrate with an oxidized nano-pillar.
Figure 6B:
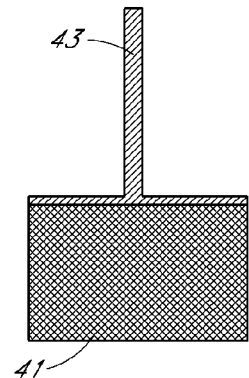
FIG. 6B illustrates a cross section of the substrate in FIG. 6A

Next, the silicon nano-pillars can be oxidized to form an un-oxidized silicon core surrounded by silicon dioxide 23. Exposing the silicon nano-pillars to an oxidizing environment forms silicon dioxide from the silicon in the nano-pillar. In some embodiments, the oxidation step can be carried out in an oxygen furnace. Oxidation of the silicon nano-pillar forms silicon dioxide from the silicon on the outer area of the silicon nano-pillar. The formation of silicon dioxide and expansion can cause strain to the silicon core of the oxidized pillars. The oxidation process can be self terminating because oxidation stops when the strain becomes too high. FIG. 1A shows a cross-section of a silicon substrate 11 with a silicon nano-pillar 12 with a thin silicon dioxide layer 13 formed on the silicon substrate 11 and silicon nano-pillar 12. FIG. 3 illustrates nano-pillars before the oxidation step. FIG. 3 also shows an oxidized nano-pillar with the remaining silicon core having a width of about 4 nm. Silicon dioxide surrounds the silicon core.

Figure 16:
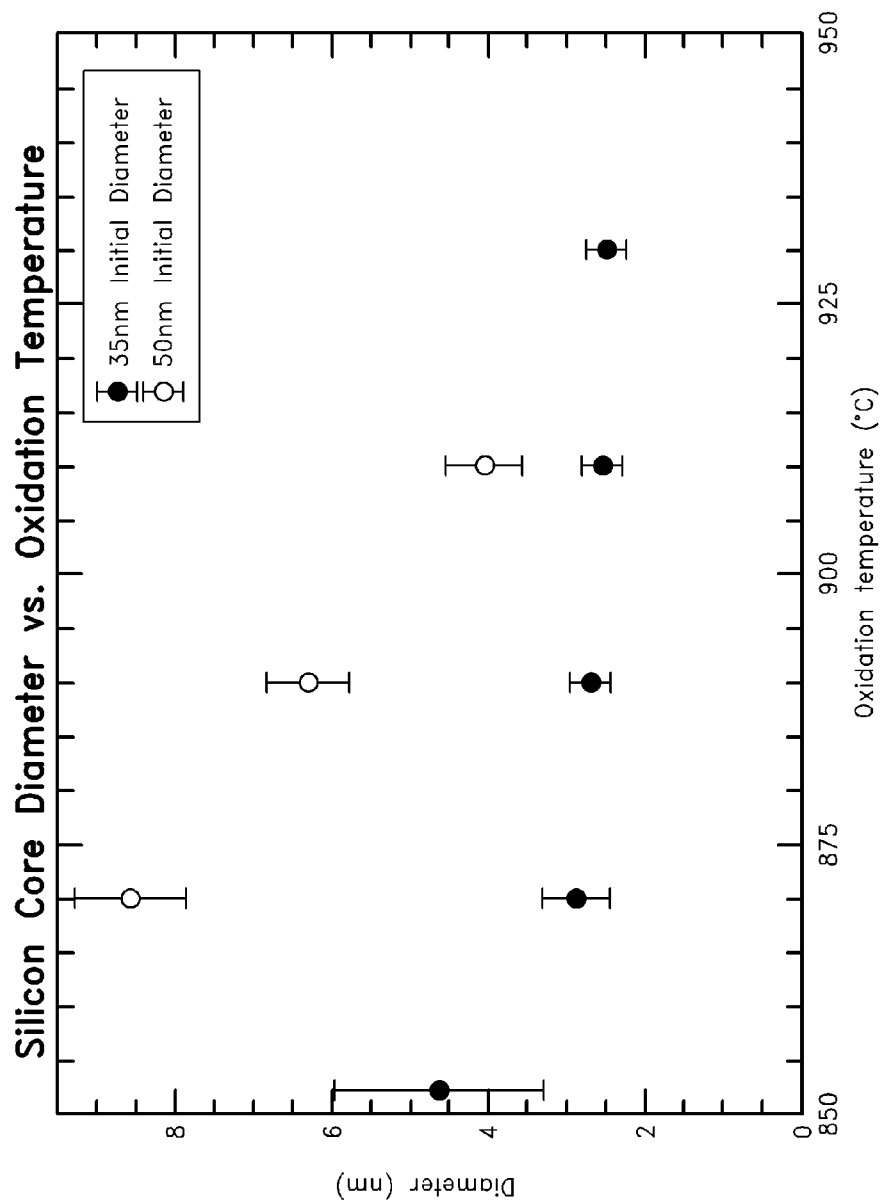
FIG. 16 is a graph illustrating the diameter of un-oxidized silicon in a nano-pillar versus the oxidation temperature used during the oxidation step.

In some embodiments, the oxidation conditions can be selected to achieve a desired amount of oxidation and, as a result, a desired width of the un-oxidized silicon at the core of the nano-pillar. For example, the silicon nano-pillar can be oxidized to a desired depth based on the oxygen furnace temperature. Applicants have discovered that the amount of silicon remaining at the core of the nano-pillar is directly related to the temperature of the oxidation step and not oxidation time. In some embodiments the temperature during the oxidation step is from about 800° C. to about 950° C. FIG. 16 is a graph illustrating the diameter of the un-oxidized silicon in the nano-pillar versus the oxidation temperature used during the oxidation step. FIG. 16 illustrates data for silicon nano-pillars having an initial diameter of about 35 nm and about 50 nm. The diameter of the silicon nano-pillar (prior to oxidation) can be selected along with the oxidation temperature to achieve a desired nano-pore size. In some embodiments the temperature during the oxidation step is above about 850° C., above about 900° C., above about 950° C., or above about 1000° C. The oxidation temperature can be selected to reliably form concentric silicon/silicon-dioxide cylinders (e.g. silicon cylinders surrounded by an oxide sheath) having a silicon core with a desired width. In some embodiments, the silicon core of the nano-pillar can have a width of less than about 10. In some embodiments, the silicon core of the nano-pillar can have a width of about 1 nm to about 5 nm after the oxidation step. In some embodiments, the silicon core of the nano-pillar can have a width of about 1 nm to about 3 nm after the oxidation step. In some embodiments, the silicon core of the nano-pillar can after oxidation can have a width of less than about 1 nm, 2 nm, 3 nm, 4 nm, 5 nm, 6 nm, 7 nm, 8 nm, 9 nm, or 10 nm.

After oxidation of the nano-pillar, one or more layers can be formed directly over the nano-pillar and substrate. In some embodiments, a conductive layer is formed over the nano-pillar 24 after it is oxidized.

In some embodiments the conductive layer comprises a metal. In some embodiments the conductive layer is deposited by metallization. In some embodiments the conductive layer comprises one or more of Pt, Cu, Au, Al, W, Ti or conductive oxides such as indium-tin-oxide (ITO) which is a mixture $In_2O_3$ and $SnO_2$. The conductive layer can be deposited in a desired pattern to form electrodes that can become part of a desired electrical circuit.

In some embodiments an insulating or dielectric layer can be deposited over the conductive layer. Examples of insulating layers include $Si_3N_4$, silicon dioxide, aluminum oxide, and other metal oxide dielectric materials.

The conductive and insulating layers can be deposited using sputtering, metallization, or vapor deposition techniques. In some embodiments, atomic layer deposition (ALD) or chemical vapor deposition (CVD) can be used to form the layers. In some embodiments, multiple conductive/insulating layers can be deposited on the substrate.

In some embodiments, a metallization layer is deposited over the substrate and pillar in a desired pattern followed by deposition of an insulating layer over the metallization layer. FIG. 1B illustrates the substrate 11 of FIG. 1A after forming a conductive metal layer 14 on top of the silicon dioxide layer followed by the deposition of an insulating layer 15 on top of the metal layer 14.

After forming the conductive layer and any insulating layer, a portion of the nano-pillar and conductive layer can be removed 25 from the substrate using physical or chemical methods to expose the silicon core. In some embodiments, a portion of the nano-pillar can be removed using mechanical polishing or similar mechanical methods. FIG. 1C is a schematic illustration showing the removal of a portion of the nano-pillar, while leaving a portion of the base of the silicon nano-pillar 12. Removing part of the nano-pillar exposes a portion of the remaining silicon nano-pillar at the substrate surface.

After removing a portion of the silicon nano-pillar, a portion of the remaining nano-pillar can be removed to form a nano-pore. In some embodiments the remaining silicon core is selectively etched to form a pore in a top surface of the substrate 26. FIG. 1D illustrates a schematic showing the substrate after selective etching of the nano-pillar to form a nano-pore 16 and an internal cavity 17 in the substrate 11. In some embodiments the silicon nano-pillar is etched back to the level of the silicon substrate. The selective etching can remove silicon relative to silicon dioxide or the other materials present on the substrate. In some embodiments, a dry etch is used to selectively remove the silicon, such as etching with $XeF_2$ or other fluorine based etchants. In some embodiments a plasma or a wet etch, such as EDP (an aqueous solution of ethylene diamine and pyrocatechol), can be used for the selective etching. The etchant can be exposed to the front polished surface where the nano-pillars were formed or the back of the substrate. In some embodiments, the etching can result in the formation of hollow silicon dioxide shells with the interior defining a nano-pore. In some embodiments, an internal cavity can be etched in the silicon substrate that is in fluid communication with the nano-pore. The etching conditions, such as time, temperature, and etchant can be selected to etch the nano-pore and a portion of the silicon substrate to create an internal cavity in the silicon substrate with a desired volume.

The size of the nano-pore is preferably sized to allow the molecule of interest to pass through, for example a single stranded DNA molecule. The size of the nano-pore is dependent on the size of the un-oxidized silicon remaining in the nano-pillar after oxidation. In some embodiments, the nano-pore has a diameter or width of about 5 nm or less. In some embodiments, the diameter or width of the pore is from about 1 nm to about 5 nm or about 1 nm to about 2 nm. In some embodiments, the nano-pore has a width of about 1 nm, 2 nm, 3 nm, 4 nm, 5 nm, 6 nm, 7 nm, 8 nm, 9 nm, or 10 nm.

Metal electrodes can be formed on the substrate before or after the selective etching step. Metal electrodes can be formed on the top or bottom of the substrate or both sides. In some embodiments metal electrodes are formed on both sides of the substrate. One or more metal electrodes can be formed on the top side of the substrate and on the bottom of the substrate. Metallization techniques known in the art can be used to deposit the metal electrodes. In some embodiments, the conductive layer or electrodes are formed on the top surface prior to forming the nano-pore. In some embodiments, the conductive layers or electrodes are formed on the bottom surface of the substrate after the internal cavity is formed. In some embodiments, the bottom electrodes can be deposited by metallization techniques prior to oxidizing the silicon nano-pillar.

In some embodiments, two electrodes are formed on a top surface of the substrate that are substantially parallel and on opposing sides of the pore. In some embodiments, two electrodes are formed on a bottom surface of the substrate that are substantially parallel and on opposing sides of the pore. Preferably the electrodes on the top surface are substantially perpendicular to the electrodes on the bottom surface of the substrate. FIG. 1E illustrates a cross section of a substrate with top electrodes formed from the metal layer 14 and a back metal layer 18 to form bottom electrodes.

In some embodiments, one or more capacitors are formed across the pore. For example, capacitors can be formed between any two wires/electrodes. In some embodiments two electrodes on opposing sides of the pore on the top or bottom of the substrate can form a single capacitor. In some embodiments, two capacitors can be used to measure the electrical properties of the material passing through the nano-pore.

Figure 11A:
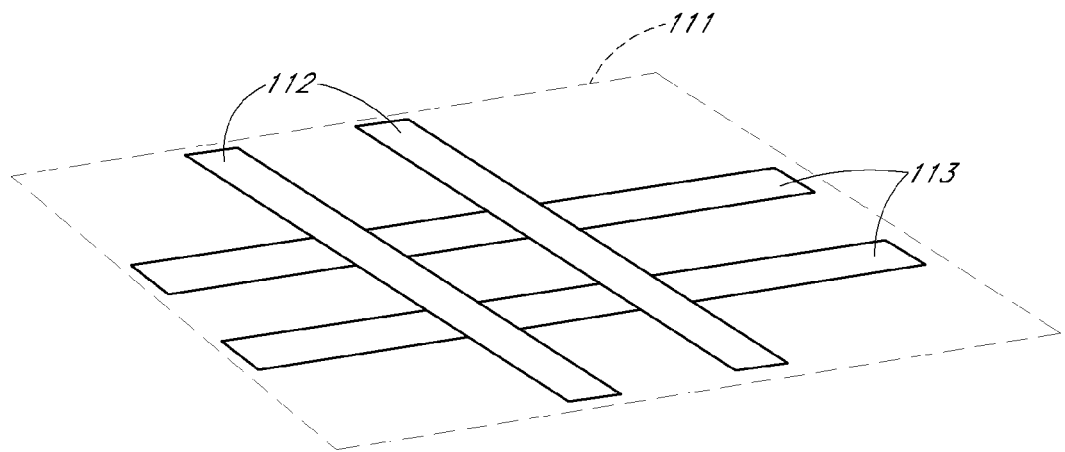
FIG. 11A illustrates a wiring pattern that can be formed on a substrate.
Figure 11B:
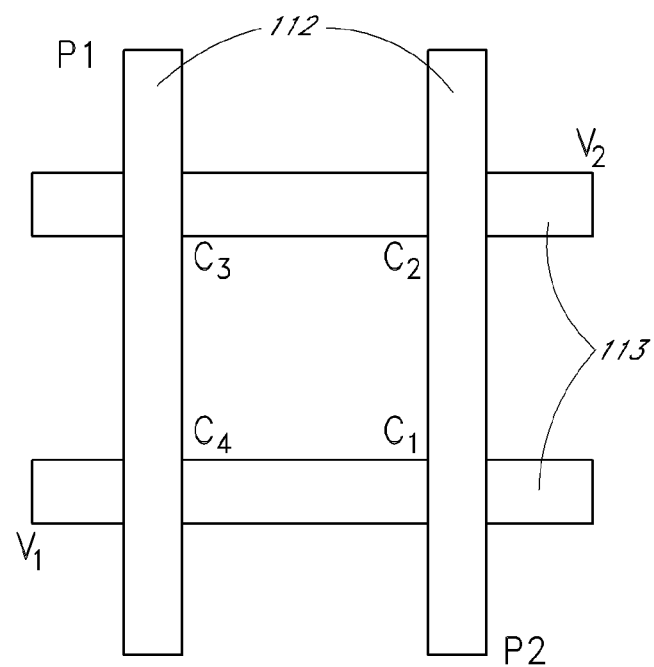
FIG. 11B is an illustration of capacitors that can be formed from the wiring pattern of FIG. 11A.

In some embodiment capacitors are formed on the device 111 at the intersections between the top and bottom electrodes with the insulating material on the substrate being between the top electrodes 113 and bottom electrodes 112 (See FIGS. 11A and 11B). In some embodiments, four capacitors can be formed from two electrodes on the top and two on the bottom of the substrate, for example see C1, C2, C3, and C4 illustrated in FIG. 11A. The nano-pore is located in the interior space between the capacitors formed by intersections of the electrodes. The center of the capacitor features a nanometer-scale pore with approximately the lateral size of the nucleic acid molecule to be sequenced. The capacitance at the four capacitors (C1-C4) can be measured as the single stranded DNA is pulled through the pore. In some embodiments an electric field can be applied between two external electrodes, for example between P1 and P2 illustrated in the circuit design shown in FIG. 12 to pull the DNA through the nano-pore. In some embodiments, a Wheatstone bridge circuit is formed on the substrate by the top and bottom electrodes. Using four capacitors with a Wheatstone bridge circuit provides greatly increased accuracy in the capacitance measurements and resulting DNA correlations.

In some embodiments, the substrate can be patterned with a hard mask in various shapes prior to forming the nano-pore. The hark mask shapes can be selected to facilitate the formation of desired circuit patterns on the substrate in subsequent metallization steps.

FIGS. 4-9 show another embodiment for forming a device for sequencing DNA. FIG. 4A illustrates the formation of a cross shaped mask 42 on a substrate 41. FIGS. 4B-9B show cross sections of FIGS. 4A-9A, respectively. FIG. 5A shows the substrate 41 after etching the patterned substrate 41 shown in FIG. 4A to form a cross shaped nano-pillar 45 on the substrate 41. Next, in FIG. 6A, the substrate is oxidized to form an oxide layer 43 on top of the substrate 41 and nano-pillar 45. As shown in FIG. 7A, the substrate is metalized to form a metal wire pattern 44 on the substrate and nano-pillar. The metallization step can be used to deposit electrical contacts or other conductive material in a pattern to make part of the desired circuit configuration. Next, a portion of the nano-pillar 45 is removed by polishing the substrate as shown in FIG. 8A. A portion of the base of the nano-pillar 45 remains on the substrate. Next, the substrate is etched to remove the remaining portions of the nano-pillar 45 at the substrate surface to form a nano-pore 46 as shown in FIGS. 9A and 9B. Although the substrate 41 is not illustrated FIG. 14C illustrates a cross section of a multi-layer structure with multiple conductive layers 143 and multiple insulating layers 142. The conductive layers 143 can be patterned to achieve a desired circuit design.

In some embodiments the substrate can contain an array of devices, for example multiple nano-pores and capacitors. In some embodiments, multiple different devices can be present on the same substrate. For example, the different devices on the substrate can have different nano-pore sizes and different capacitor configurations. In some embodiments the devices are spaced about 100 nm to about 150 nm apart. The multiple devices on the substrate can be used to sequence multiple nucleic acids, molecules, and/or nanoparticles at the same time.

Methods for Sequencing DNA

Methods are disclosed herein for sequencing DNA. Although, the methods are disclosed in terms of DNA, the methods can be applied to RNA, other nucleic acids, and other molecules. The methods disclosed herein can result in improved fidelity and faster nucleotide identification. Individual DNA nucleotides occupy a voxel space of about 2 nm by 2 nm by 2 nm. It is very difficult to measure or address a single base pair at a time because of the small size. The small size can be a problem in methods using purely physical detection as nearby nucleotides can contribute to the signal from the desired nucleic acid by contributing to a decrease in current in a current obstruction method of detection and by sampling the fringing field in a capacitive detection mechanism.

In some embodiments, the DNA sample to be sampled can be denatured, if desired.

The DNA sample can be pulled through the nano-pore of the devices disclosed herein. For example, an electric filed can be applied across the nano-pore to pull the DNA sample through the nano-pore. In other embodiments, the sample can be moved through by other means, such as enzymatically. The capacitance is measured as the DNA sample passes through the pore. Other electrical properties can also be measured and tuned to facilitate the sequencing of the DNA sample. Enzymes can be used to cleave portions of the DNA sample that can then be measured or to facilitate the measurement of the DNA sample in other ways, such as holding the DNA in the pore. The capacitance measurements made for the DNA sample can then be correlated to the corresponding nucleotides to sequence the DNA sample.

Figure 10:
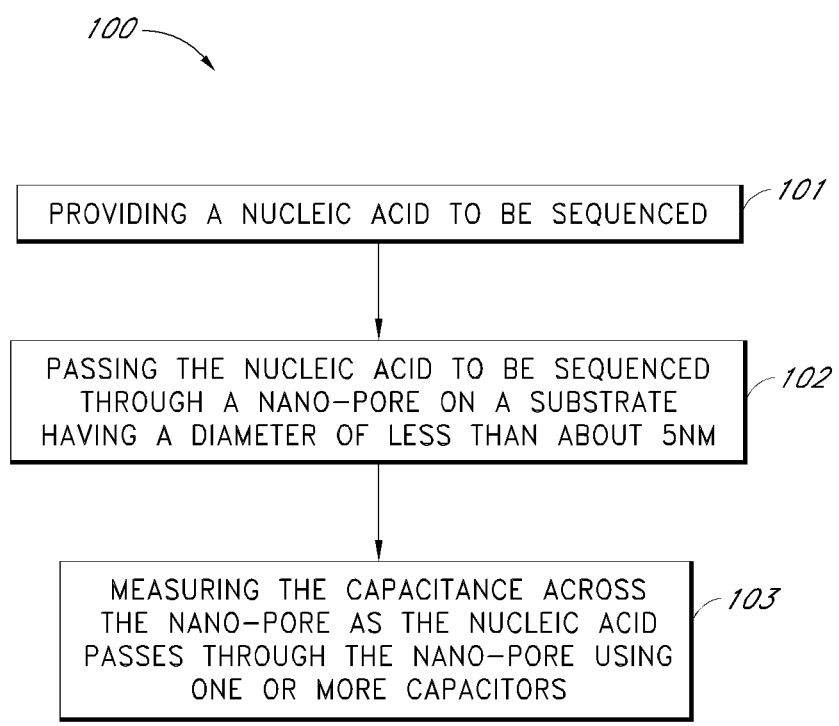
FIG. 10 is a flow chart illustrating a method for sequencing DNA.

FIG. 10 is a flow chart illustrating a method for sequencing a nucleic acid in one embodiment 100. The nucleic acid to be sequenced is provided 101. Next, the nucleic acid to be sequenced is passed through a nano-pore on a substrate having a diameter of less than about 5 nm 102. The capacitance across the nano-pore is measured as the nucleic acid passes through the nano-pore using one or more capacitors 103.

The base pairs of a single-stranded (e.g. unwound) DNA polymer can be interrogated while the molecule is pulled through nano-pores formed in a silicon substrate. In some embodiments, an electric field can be applied to pull the DNA molecules through the pore. In some embodiments, the circuits and capacitors described herein are formed around the pore. The changes in various electrical properties can be measured as the DNA molecule moves through the nano-pore. For example, as the base pairs pass through the pore, alternating current (AC) and small signal capacitance measurements can be made.

In some embodiments, the capacitance is measured as the DNA molecule passes through the nano-pore.

In some embodiments, the voltage is measured as the DNA molecule passes through the nano-pore.

In some embodiments, the amount of current or alternating current is measured as the DNA molecule passes through the nano-pore.

In some embodiments, the tunneling current is measured as the DNA molecule passes through the nano-pore.

In some embodiments, the ionic current is measured as the DNA molecule passes through the nano-pore. The geometry of individual base pairs can result in unique changes in the amount of ion flux though the nano-pores. This change can be described as a "blocking" current.

The alternating current and frequency can be varied to improve the data collection. The small size of the nano-pores and the capacitors used herein can result in improved signal to noise ratio for the capacitance data collected during the sequencing. The capacitance measurement can also be performed at higher frequencies approaching GHz frequencies. The frequencies can also be modulated to improve the resolution of the data collection.

In some embodiments a direct current (DC) can be used to facilitate the movement of the DNA strand through the nano-pore. In some embodiments, AC current can be used along with a DC bias when passing the DNA strand through the nano-pore.

The decreased size of the individual devices and pores can allow for many devices to be located within a small area. In some embodiments, the devices disclosed herein can be integrated with on-chip amplification circuitry to further enhance signal/noise results. In some embodiments, multiple DNA molecules can be measured in parallel on the same substrate using multiple individual devices. In some embodiments an array of devices comprising nano-pores can be formed on the silicon substrate. Many strands of DNA can be sequenced simultaneously in parallel using a single substrate comprising an array of sequencing devices.

In some embodiments, the DNA molecule or segment can be interrogated multiple times while it passes through the pore. For example, the current can be applied to pull the DNA molecule through the pore. The current can then be reversed to pull the DNA molecule through the pore in the opposing direction. Current reversal can produce an alternating directional flow of the ions in solution surrounding the DNA molecule. The capacitance can be measured for the DNA molecule going forward through the pore and also going backwards for the pore. The frequency of the signal can be optimized to enable ions to move through the pore and keep the single-stranded DNA molecule within the pore for long enough to measure the capacitance changes as well as the "blocking" current that can result from contributions of the chemical and Van der Waals interaction between the DNA and the surrounding ions.

In some embodiments, the frequency can be varied between multiple frequencies to produce electrical measurements that are specific enough to correspond to signatures for the nucleic acids within the volume of the pore. The frequency can be selected to move the DNA molecule through the pore at a desired speed. The frequency of the electrical measurements can also be selected based on the rate at which the DNA molecule passes through the pore to optimize the accuracy of the sequencing results.

The number of nucleotides that fit within the volume of the pore can be varied based on the size of the nano-pore. In some embodiments about one to about five nucleotides can fit in the volume defined by the nano-pore. Preferably about four nucleotides can fit in the volume of the nano-pore. The electrical measurements correspond to the nucleotides present in the volume of the nano-pore at the time the electrical measurements are made.

In some embodiments, the measurement of the blocking current can be used in conjunction with the capacitance measurements and other electrical measurements to help determine the nucleotides present in the pore.

In some embodiments, the methods disclosed herein can be used to achieve high selectivities and low error rates for the sequencing of the DNA molecules. The error rate and accuracy can meet the levels desired for most medical and biological applications.

In some embodiments, the improved alternating current measurement is facilitated by locating the electrical contacts or electrodes very close to the pore by the fabrication methods disclosed herein. The location of the electrodes can reduce the series resistance and facilitate higher frequency measurements. In some embodiments the electrodes can be located from about 5 nm to about 50 nm from the nano-pore.

In some embodiments, the use of multiple capacitors in a multi-layered structure can facilitate low-noise measurements and confinement of the electrostatic field in the capacitor. In some embodiments, the layers above and below the measurement electrode can also be grounded to provide efficient electromagnetic shielding from stray fields and lower the divergence of the electrostatic field of the capacitor volume.

In some embodiments, multiple molecules can be measured in the pore at the same time. Additional methods for measuring DNA nucleotides can be used in conjunction with the methods and devices disclosed herein. In some embodiments, the individual nucleotides can be measured by locating an enzyme at the entrance of the micro-fabricated pore. The enzyme can cut the individual base-pairs from the DNA molecule and facilitate the transfer of individual base pairs through the pore. In some embodiments the enzyme can cut the single-stranded DNA molecule into individual nucleotides. In some embodiments, enzymes such as alpha helicase and RNA and DNA polymerases can be used to control DNA movement through the nano-pore or to cleave desired sections of the DNA strand.

The individual nucleotides can be individually interrogated passing through the micro-fabricated pore/capacitor device. In some embodiments, the enzymes can hold sections of the DNA for several milliseconds in order to obtain measurable signals for the portions of the DNA molecule moving through the pore. In these embodiments, the speed for sequencing the DNA is increased, however; the complexity of signal processing and analysis is reduced.

Circuits for Measuring Capacitance

Circuits for measuring the capacitance across the pore are disclosed herein. The processing steps disclosed herein can be used to form circuits on the substrate, including capacitors.

The capacitance across the pore can be measured by the capacitors adjacent to the pore as the DNA molecule passes through the pore. In some embodiments, the measurement of capacitance can be conducted within a solution containing DNA molecules, and the capacitance changes resulting from nucleotides or single stranded DNA molecules passing through the pores can be monitored by measuring the capacitance. Different basepairs or combinations of basepairs passing through the pore create varying capacitance readings for the capacitors, In some embodiments, a single capacitor is used to measure the capacitance across the pore. In some embodiments, two capacitors are used to measure the capacitance across the pore. In some embodiments, four capacitors can be used, for example C1, C2, C3, and C4 illustrated in FIGS. 11B and 12.

Sequencing DNA can be slow when attempting to measure one nucleotide at a time. Additionally, interference, for example, from adjacent basepairs or other DNA molecules can adversely affect the accuracy and precision of these methods. The circuits disclosed herein can result in improved accuracy and precision for sequencing the DNA, including sequencing multiple base pairs at once.

Figure 12:
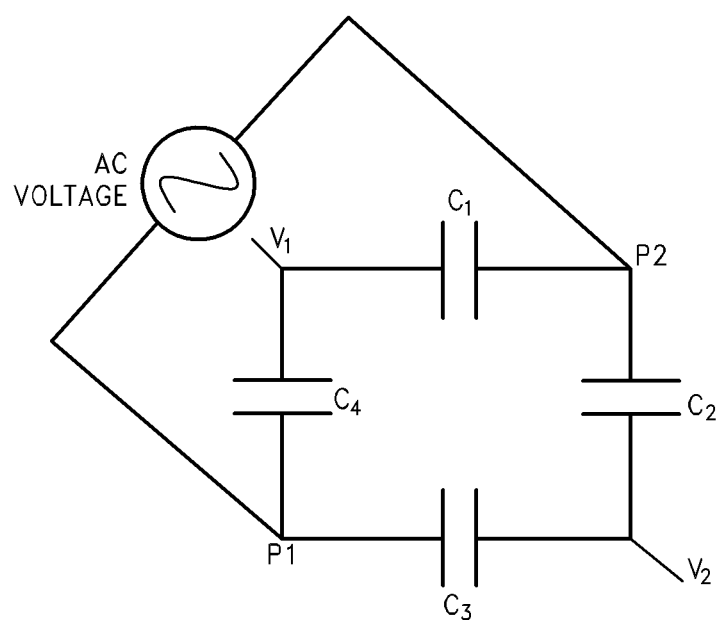
FIG. 12 shows a circuit that can be formed from the wiring configuration illustrated in FIGS. 11A and 11B.

In some embodiments, a capacitance bridge circuit can be used to increase the sensitivity of a capacitance measurement. FIGS. 11A, 11B, and 12 describe embodiments of a capacitance bridge circuit that can be used to reduce the noise of the individual measurement, and provides a convenient way to convert capacitance changes into measured voltage readings.

In some embodiments, the frequency of the applied AC voltage can be changed to tune the circuit to result in improved contrast for the readings from the different nucleotides.

In some embodiments the noise in local measurements of capacitance can be significantly reduced by locating the circuit and electronic components in close proximity to the pore.

In some embodiments the desired circuit pattern or a portion of the desired circuit pattern is deposited by metallization. A mask pattern and photolithography can be used to deposit the desired circuit pattern. In some embodiments, the bridge circuit can be fabricated through lithography during the metallization steps using a mask pattern. The metallization lines can be connected on both sides of the silicon structure to circuits that are used to monitor changes in voltage resulting in changes in the capacitance. An applied electrical field can be used to pull the DNA molecules through the pores. The capacitance can be measured as the DNA molecules pass through the pore. A change in the variable capacitor C1 translates into a change in the measured voltage of the capacitance bridge between V1 and V2 (see FIGS. 11B and 12).

Figure 7A:
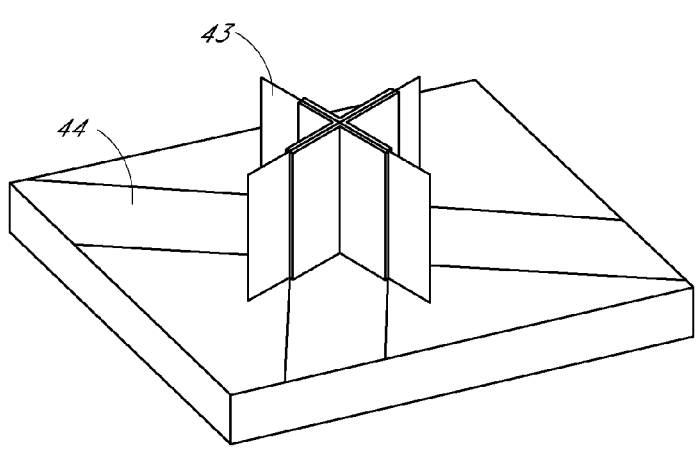
FIG. 7A illustrates a substrate with a nano-pillar.
Figure 7B:
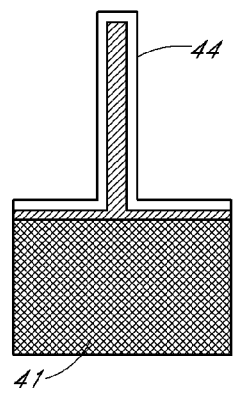
FIG. 7B illustrates a cross section of the substrate in FIG. 7A.

The metallization steps disclosed herein can be used to deposit various circuit designs on the top and bottom of the silicon dioxide membrane. Different mask configurations can be used to form various circuit designs. In some embodiments the lithography and metallization steps enable the construction of several capacitors that are oriented in different directions and self-aligned to the same pore. For example, FIGS. 4-9 use a cross shaped hard mask to form a cross shaped fin. The metal can be deposited over a thin micro-fabricated fin (FIG. 7A). The fin can be used to interrupt the contact of the metallization layer with the surface of the substrate and subsequently removed (FIG. 8A).

In some embodiments orthogonal capacitors in quadrupole arrangements can be used. For example, FIGS. 9A and 17A show two orthogonal capacitors in a quadrupole arrangement. Other configurations and arrangements can be used by modifying the shape of the etched fin structure. Different hard mask patterns can be used to facilitate the formation of desired circuit geometry. For example, hexapole or octupole geometries can also be used.

Multiple in-plane capacitors can be used to interrogate the molecule in different directions. For example, the relative difference in dielectric constant can be measured in multiple directions around and across the pore.

In some embodiments, multiple metallization layers can be used. In some embodiments multiple metallization layers can be used with one or more insulating layers between the metallization layers. In some embodiments, three or more metallization layers can be used. Thin insulating layers can be deposited between the metallization layers to create multiple capacitor structures. The multilayer capacitor structures can be deposited using sputter deposition, atomic layer deposition, CVD, or electrodeposition processes.

Figure 14A:
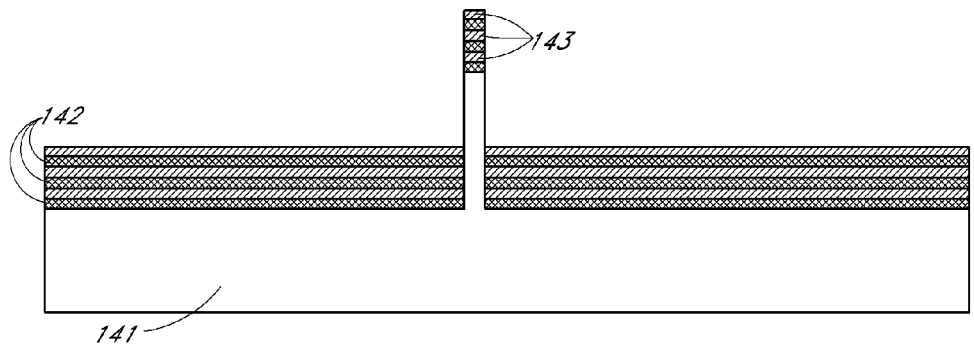
FIGS. 14A-C illustrate a cross-section of a substrate during various processing steps.
Figure 14B:
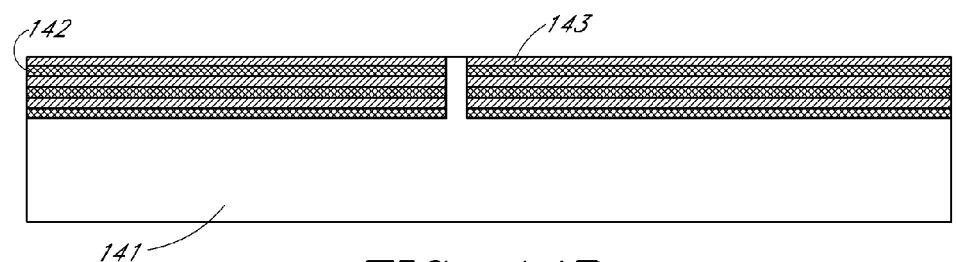
Figure 14C:
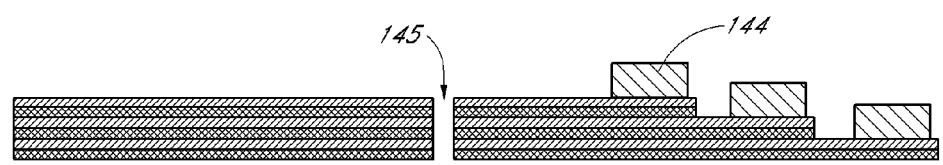
Figure 15A:
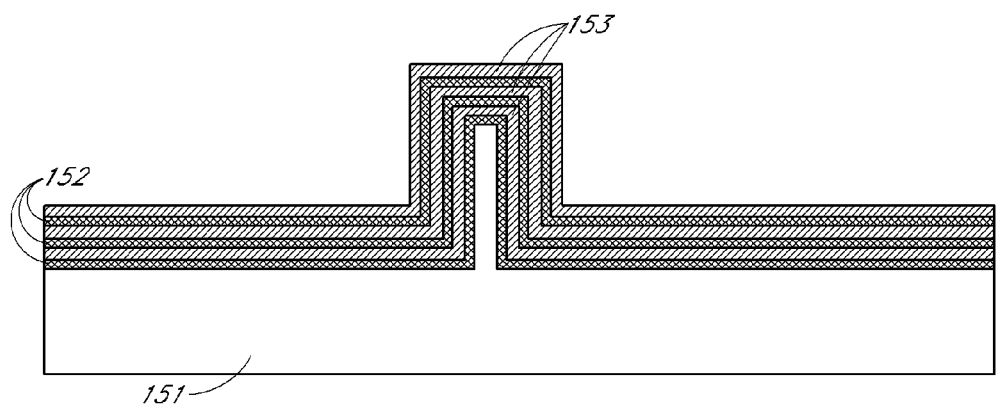
FIGS. 15A-C illustrate a cross-section of a substrate during various processing steps.
Figure 15B:
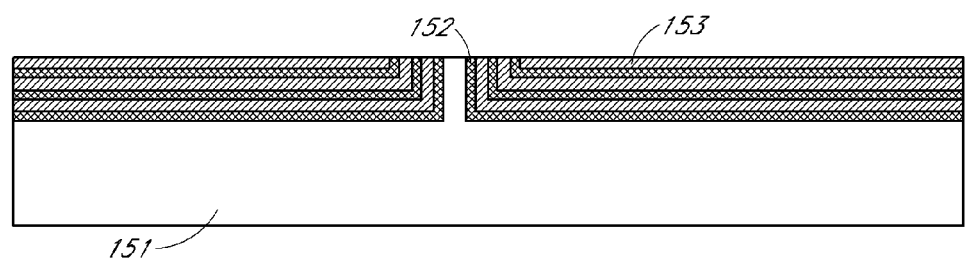
Figure 15C:
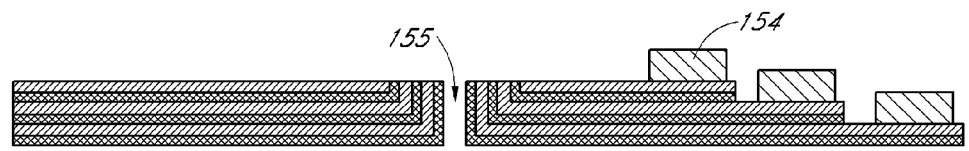

FIGS. 14A-C and 15A-C illustrate schematic cross sections of multilayer capacitor structures. FIGS. 14A-C illustrate multiple conductive layers 143 and multiple insulating layers 142 formed over a substrate 141. Etching the silicon substrate 141 forms a nano-pore 145. Electrical contacts 144 can be added to the conductive layers 143. FIGS. 15A-C illustrate multiple conformal conductive layers 152 and multiple conformal insulating layers 153 formed over a substrate 151. Etching the silicon substrate 151 forms a nano-pore 155. Electrical contacts 154 can be added to the conductive layers 153. FIGS. 14A-C illustrate using directional deposition techniques, such as sputtering, that can be used to deposit materials with smaller grain sizes instead of conformal deposition techniques, e.g. FIGS. 15A-C. In some embodiments, directional deposition techniques are preferred because of the resulting structure.

Correlating Capacitance to Base Pair Sequence

The methods described above can be used to generate capacitance values for the DNA material passing through the pore. The capacitance and other electrical data collected when the DNA passes through the pore can be correlated to extrapolate the sequence of base pairs going through the pore with a high degree of accuracy.

One of the major problems during the measurement of DNA sequences lies in the area of quality control of the measurement. Most of the time, measured data obtained from DNA sequencing approaches provides some confidence in the measurement from previous experience and calibration, but it is difficult to provide accurate confidence limits to the background measurements in real time. The methods disclosed herein provide improved accuracy and precision for real time sequencing of DNA molecules.

In some embodiments a single capacitor is used to measure the capacitance across the pore for the molecule in the pore. In some embodiments, four capacitors are used to measure the capacitance.

In some embodiments, methods for calibrating an apparatus for sequencing nucleic acids are provided. The methods include providing a nucleic acid with a known nucleotide sequence to an apparatus comprising a nano-pore and multiple capacitors. In some embodiments the capacitance of the multiple capacitors is measured while passing the strand of DNA through the nano-pore. The capacitance values are correlated to the known sequence of the nucleic acid to create a reference or "look up" table for the apparatus. The correlation data can then be used to correlate capacitance data for a nucleic acid to the nucleotide sequence.

In some embodiments the blocking current, capacitance, and/or tunneling currents can be used to determine individual basepair sequences within long DNA chains. In some embodiments a single nucleotide or base pair can be measured within the pore at a time. In some embodiments, multiple nucleotides can be measured within the pore. In some embodiments one, two, three, four, five, six, seven, eight, nine, or ten nucleotides can fit within the volume of the nano-pore.

In some embodiments, DNA strands having a known sequence ("calibration" DNA) can be used to calibrate the DNA sequencing device. For example, the electrical signals for a particular device configuration can be calculated by passing calibration DNA through the pore. The use of calibration DNA can improve the confidence in the precision of the measurements by the sequencing device. The calibration DNA can be artificially synthesized with desired sequences. For example, simple sequences of multiple basepairs such as AAAACCCCTTTTGGGGAAAC-CCTTTGGGAACCTTGGACTG . . . can be used to generate well-recognizable signatures and determine the accuracy with which multiple basepairs are measured.

In some embodiments, the calibration DNA can be sequenced with the real samples to provide time, accuracy, and resolution limit information in real time. Sequencing of calibration standards can also be used to determine the sequencing speed of a particular device configuration. In some embodiments the DNA sequencing device's bias between different base pairs can be detected, for example by comparing the efficiency of measuring a GCGCGCGCGC sequence to an ATATATATAT sequence.

The electrical properties for single nucleotides and multiple nucleotides passing through the pore can be determined using the calibration DNA. The signals for single and multiple nucleotides can be determined using the calibration DNA with the data collected for many different combinations of nucleotides passing through the pore. The data can be collected for all of the different nucleotide combinations passing through the pore to generate a "look up" table.

In some embodiments, the device can be calibrated using 'register comparison" methods. For example, a minimum number of base pairs that can be sampled by the detection mechanism can be determined and the device is then calibrated by determining the signal associated with each unique base pair combination. For example, if the detection mechanism sampled 5 base pairs simultaneously then the device would contain a look-up table of the 45 possible signals associated with measuring 5 base pairs.

The device can be used to sequence the DNA sample using the look up tables or correlation data. The device can measure the signal in the pore and correlate that to a specific sequence of DNA in the pore. The first measurement could be taken to determine the base pairs present in the pore, without knowing the corresponding order. For example, the first reading could correspond to a nucleotide group of ATGAC (in no particular order). The device would then shift the DNA down by a base pair and take a measurement again and then compare the two. For example, the second measurement could correspond to TGACT. The two signals and their corresponding base pair combinations can be compared. In this example it would be identified that the A nucleotide was dropped and the T nucleotide was gained when the DNA was shifted down by one base pair. This method of taking differential measurements allows the DNA to be sequenced faster and with greater fidelity and requires a much less intricate fabrication mechanism.

In some embodiments, the sequencing can be performed along with alternating the current to generate forward and backwards readings of the samples and to improve the accuracy and precision of the DNA measurements.

Example 1

A hard mask of aluminum oxide was sputtered onto a silicon substrate to form nano-disks having a diameter of about 35 nm spaced evenly apart. A mixture of $SF_6/C_4F_8$ was used to etch the silicon substrate around the hard mask, thereby forming a number of silicon nano-pillars with diameters of about 35 nm. FIG. 3 shows silicon nano-pillars after removal of the hard mask. After removing the aluminum oxide hard mask using hydrofluoric acid, the nano-pillars were oxidized in a furnace at a temperature of above 850° C. The methods in this example resulted in an un-oxidized silicon nano-pillar core having a diameter of about 2 nm. Copper was deposited over the substrate and oxidized nano-pillars by DC magnetron sputter deposition. Next, mechanical polishing was performed to remove portions of the nano-pillars in order to expose the un-oxidized silicon core at the base of the nano-pillar. $XeF_2$ was used to etch the remaining un-oxidized silicon core to form a nano-pillar with a diameter of about 2 nm. The $XeF_2$ was also used to etch a portion of the backside of the substrate to form an internal cavity in fluid communication with the nano-pore.

Example 2

A hard mask is applied to a silicon substrate in a desired pattern. The silicon substrate is then etched to create a raised pattern in the shape of the hard mask. Next, the hard mask is removed to leave raised silicon structures on the substrate. The silicon substrate and raised silicon structures are then oxidized in a furnace at a temperature of above about 850° C. The silicon structures or pillars are oxidized such that a silicon core having a width of about 1 nm remains after oxidation. Next, a conductive metal layer is deposited on the substrate and nano-pillars in a desired pattern using a metallization process. Mechanical polishing is used to polish the top surface of the substrate to remove the raised silicon structures or nano-pillars. A portion of the un-oxidized silicon nano-pillar remains. Next, $XeF_2$ is used to etch the remaining un-oxidized silicon nano-pillar to create a nano-pore having a diameter of about 1 nm. $XeF_2$ is also used to etch a small internal cavity in the silicon substrate. Metallization steps are used to form two substantially parallel electrodes on opposing sides of the nano-pore. Two electrodes are formed on top of the substrate and below the nano-pore. The top and bottom electrodes are substantially perpendicular to each other thereby forming four capacitors.

A single strand of DNA having a known sequence is passed through the nano-pore. An electric field is applied to the DNA sample to facilitate moving the DNA strand through the pore. Capacitance measurements are continuously taken with a high frequency, such that measurements are taken of the DNA strand as each nucleotide of the strand enters/exits the volume of the nano-pore. The capacitance readings are then correlated to the corresponding nucleotide sequences within the volume of the nano-pore when the measurements were taken.

A single strand of DNA to be sequenced is then passed through the nano-pore. The capacitance values are measured as each nucleotide exits the nano-pore. The capacitance data is then correlated to the corresponding nucleotides present in the volume of the nano-pore when the measurements were taken. The nucleotide data can be analyzed to determine the sequence of the measured DNA strand.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. In addition, while one variation of the invention has been shown and described in detail, other modifications, which are within the scope of this invention, will be readily apparent to those of skill in the art based upon this disclosure. It is also contemplated that various combinations or sub-combinations of the specific features and aspects of the embodiment may be made and still fall within the scope of the invention. Thus, it is intended that the scope of the present invention herein disclosed should not be limited by the particular disclosed embodiment described above, but should be determined only by a fair reading of the claims that follow.

What is claimed is:

1. A method for sequencing a nucleic acid, comprising:
providing a nucleic acid to be sequenced;
passing the nucleic acid to be sequenced through a nano-pore on a substrate, the nano-pore having a diameter of less than about 5 nm; and
the nano-pore measuring the capacitance across the nano-pore as the nucleic acid passes through the nano-pore using one or more capacitors,
wherein the substrate has two top electrodes that are substantially parallel to each other and on opposing sides of the nano-pore on the top surface of the substrate and two bottom electrodes that are substantially parallel to each other and on opposing sides of the nano-pore on the bottom surface of the substrate, and wherein the top electrodes are substantially perpendicular to the bottom electrodes and each intersection of the top and bottom electrodes forms a capacitor.

2. The method of claim 1, further comprising correlating the capacitance measurements to known capacitance values for specific nucleic acids.

3. The method of claim 1, wherein the nano-pore has a diameter of less than about 2 nm.

4. The method of claim 1, wherein the nucleic acid is DNA.

5. The method of claim 4, wherein the DNA comprises one of RNA, single stranded DNA, or double stranded DNA.

6. The method of claim 1, wherein the nano-pore is sized to fit about 5 or less nucleotides within the volume of the nano-pore.

7. The method of claim 4, wherein after the capacitance is measured the DNA in the pore shifts by one nucleotide and the capacitance is measured again.

8. The method of claim 4, further comprising providing alternating current to move the DNA forwards and backwards through the nano-pore.

9. The method of claim 1, wherein an electric field is provided to pull the nucleic acid through the pore.

10. The method of claim 4, further comprising using an enzyme to control the DNA passing through the pore.

11. The method of claim 1, wherein an enzyme is used to cleave portions of the nucleic acid.

12. The method of claim 1, wherein four capacitors are formed by the top and bottom electrodes.

13. The method of claim 1, wherein the nucleic acid to be sequenced has a known nucleotide sequence; further comprising correlating the capacitance values to the known nucleotide sequence of the nucleic acid.

14. The method of claim 13, wherein the apparatus has four capacitors adjacent to the nano-pore.

15. The method of claim 13, wherein one to five nucleotides can fit in an internal volume of the nano-pore.

16. The method of claim 15, wherein the known nucleotide sequence contains all of the possible sequence permutations for the number of nucleotides that can fit in the internal volume of the nano-pore.

* * * * *

```
                        SEQUENCE LISTING

<160> NUMBER OF SEQ ID NOS: 5

<210> SEQ ID NO 1
<211> LENGTH: 40
<212> TYPE: DNA
<213> ORGANISM: Artificial Sequence
<220> FEATURE:
<223> OTHER INFORMATION: Exemplary sequence

<400> SEQUENCE: 1
aaaacccctt ttggggaaac cctttgggaa ccttggactg                              40

<210> SEQ ID NO 2
<211> LENGTH: 10
<212> TYPE: DNA
<213> ORGANISM: Artificial Sequence
<220> FEATURE:
<223> OTHER INFORMATION: Exemplary sequence

<400> SEQUENCE: 2
gcgcgcgcgc                                                              10

<210> SEQ ID NO 3
<211> LENGTH: 10
<212> TYPE: DNA
<213> ORGANISM: Artificial Sequence
<220> FEATURE:
<223> OTHER INFORMATION: Exemplary sequence

<400> SEQUENCE: 3
atatatatat                                                              10

<210> SEQ ID NO 4
<211> LENGTH: 5
<212> TYPE: DNA
<213> ORGANISM: Artificial Sequence
<220> FEATURE:
<223> OTHER INFORMATION: Exemplary sequence

<400> SEQUENCE: 4 atgac                                                                    5

<210> SEQ ID NO 5
<211> LENGTH: 5
<212> TYPE: DNA
<213> ORGANISM: Artificial Sequence
<220> FEATURE:
<223> OTHER INFORMATION: Exemplary sequence

<400> SEQUENCE: 5 tgact                                                                    5
```